United States Patent
Zhang et al.

(10) Patent No.: US 11,375,906 B2
(45) Date of Patent: Jul. 5, 2022

(54) METHOD AND APPARATUS FOR DETECTING FETAL BLOOD OXYGEN SATURATION, COMPUTER-READABLE STORAGE MEDIUM AND COMPUTER DEVICE

(71) Applicant: BOE Technology Group Co., Ltd., Beijing (CN)

(72) Inventors: Xun Zhang, Beijing (CN); Yang Han, Beijing (CN); Guangfei Li, Beijing (CN); Hui Du, Beijing (CN); Siyang Liang, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 189 days.

(21) Appl. No.: 16/768,367

(22) PCT Filed: Dec. 25, 2019

(86) PCT No.: PCT/CN2019/128320
§ 371 (c)(1),
(2) Date: May 29, 2020

(87) PCT Pub. No.: WO2020/147534
PCT Pub. Date: Jul. 23, 2020

(65) Prior Publication Data
US 2021/0204820 A1 Jul. 8, 2021

(30) Foreign Application Priority Data
Jan. 18, 2019 (CN) .......................... 201910048957.6

(51) Int. Cl.
*A61B 5/0205* (2006.01)
*A61B 5/1464* (2006.01)
(Continued)

(52) U.S. Cl.
CPC ........ *A61B 5/0205* (2013.01); *A61B 5/02411* (2013.01); *A61B 5/02416* (2013.01);
(Continued)

(58) Field of Classification Search
CPC . A61B 5/1455; A61B 5/14551; A61B 5/1464; A61B 5/0205; A61B 5/02411; A61B 5/02416
See application file for complete search history.

(56) References Cited

U.S. PATENT DOCUMENTS 9,757,058 B2 * 9/2017 Ray .................... A61B 5/14552
2004/0116789 A1 6/2004 Boas et al.
2011/0218413 A1 9/2011 Wang et al.

FOREIGN PATENT DOCUMENTS

CN 102988036 A 3/2013
CN 103381094 A 11/2013
(Continued)

OTHER PUBLICATIONS

May 27, 2020—(CN) Second Office Action Appn 201910048957.6 with English Translation.
(Continued)

*Primary Examiner* — Eric F Winakur
(74) *Attorney, Agent, or Firm* — Banner & Witcoff, Ltd.

(57) ABSTRACT

A method for detecting fetal blood oxygen saturation, including: using at least two detection light of different wavelengths, to irradiate a fetus in an examined pregnant woman's abdomen in a time-sharing manner and acquiring first photoplethysmography signals corresponding to the abdomen under irradiation of the respective wavelengths of detection light, and to irradiate a detection site except the examined pregnant woman's abdomen in a time-sharing manner and acquiring second photoplethysmography signals corresponding to the detection site under irradiation of the
(Continued)

respective wavelengths of the detection light; determining a target photoplethysmography signal of the fetus that corresponds to the detection light of each wavelength, according to the first photoplethysmography signals and the second photoplethysmography signals that correspond to the detection light of each wavelength; and determining the fetal blood oxygen saturation, according to respective target photoplethysmography signals determined.

11 Claims, 4 Drawing Sheets

(51) Int. Cl.
  *A61B 5/024* (2006.01)
  *A61B 5/1455* (2006.01)
  *A61B 5/00* (2006.01)
(52) U.S. Cl.
  CPC ........ *A61B 5/1464* (2013.01); *A61B 5/14551* (2013.01); *A61B 5/6823* (2013.01)

(56) References Cited

FOREIGN PATENT DOCUMENTS

| | | |
|---|---|---|
| CN | 104224197 A | 12/2014 |
| CN | 104490389 A | 4/2015 |
| CN | 106859626 A | 6/2017 |
| CN | 108420441 A | 8/2018 |
| CN | 109528216 A | 3/2019 |
| EP | 0522674 A2 | 1/1993 |

OTHER PUBLICATIONS

Gao, et al., "The Monitoring of Fetal Blood Oxygen Saturation and its Clinical Significance", Dalian Obstetrics and Gynecology Hospital, Dalian, Liaoning Province, 116033, Chinese Book Classification No. R715.7, Document Identification Code A, Article No. 1001-4411 (2005) 05-0596-02.

* cited by examiner

METHOD AND APPARATUS FOR DETECTING FETAL BLOOD OXYGEN SATURATION, COMPUTER-READABLE STORAGE MEDIUM AND COMPUTER DEVICE The application is a U.S. National Phase Entry of International Application No. PCT/CN2019/128320 filed on Dec. 25, 2019, designating the United States of America and claiming priority to Chinese Patent Application No. 201910048957.6 filed on Jan. 18, 2019. The present application claims priority to and the benefit of the above-identified applications and the above-identified applications are incorporated by reference herein in their entirety.

TECHNICAL FIELD

Embodiments of the present disclosure relate to a technical field of detection, and more particularly, to a method and an apparatus for detecting fetal blood oxygen saturation, a computer-readable storage medium and a computer device.

BACKGROUND

Fetal blood oxygen saturation is a physiological index that relatively directly reflects a fetal life state. Since there is currently no instrument or device for detecting fetal blood oxygen saturation in an effective non-invasive manner, and a fetal heart rate monitor is used for monitoring a fetal physiological state, medical personnel usually can only rely on the fetal heart rate monitor for monitoring. However, use of the fetal heart rate monitor is only an indirect monitoring method, which may lead to inaccurate fetal blood oxygen saturation detected.

SUMMARY

Embodiments of the present disclosure provide a method and an apparatus for detecting fetal blood oxygen saturation, a computer-readable storage medium and a computer device, to improve accuracy of fetal blood oxygen saturation detected.

At least one embodiment provides a method for detecting fetal blood oxygen saturation in this disclosure, comprising:

using at least two detection light of different wavelengths, to irradiate a fetus in an examined pregnant woman's abdomen in a time-sharing manner and acquiring first photoplethysmography signals corresponding to the abdomen under irradiation of the respective wavelengths of detection light, and to irradiate a detection site except the examined pregnant woman's abdomen in a time-sharing manner and acquiring second photoplethysmography signals corresponding to the detection site under irradiation of the respective wavelengths of the detection light;

determining a target photoplethysmography signal of the fetus that corresponds to the detection light of each wavelength, according to the first photoplethysmography signals and the second photoplethysmography signals that correspond to the detection light of each wavelength; and determining the fetal blood oxygen saturation, according to respective target photoplethysmography signals determined.

For example, in the method for detecting fetal blood oxygen saturation provided in the at least one embodiment of this disclosure, the determining the target photoplethysmography signal of the fetus that corresponds to the detection light of each wavelength, according to the first photoplethysmography signals and the second photoplethysmography signals that correspond to the detection light of each wavelength, comprises:

determining a target frequency domain signal of the fetus that corresponds to the detection light of each wavelength, according to the first photoplethysmography signals and the second photoplethysmography signals that correspond to the detection light of each wavelength; determining a corresponding fetal heart rate according to a preset rule; and determining the target photoplethysmography signal of the fetus that corresponds to the detection light of each wavelength, according to the corresponding fetal heart rate determined and respective target frequency domain signals.

For example, in the method for detecting fetal blood oxygen saturation provided in the at least one embodiment of this disclosure, the determining a corresponding fetal heart rate according to the preset rule, comprises:

determining a fetal heart rate corresponding to the detection light of each wavelength, according to the target frequency domain signal of the fetus that corresponds to the detection light of each wavelength; and the determining the target photoplethysmography signal of the fetus that corresponds to the detection light of each wavelength, according to the corresponding fetal heart rate determined and the respective target frequency domain signals, comprises:

determining the target photoplethysmography signal of the fetus that corresponds to the detection light of each wavelength, according to the fetal heart rate and the target frequency domain signal corresponding to the detection light of each wavelength.

For example, in the method for detecting fetal blood oxygen saturation provided in the at least one embodiment of this disclosure, the determining the fetal heart rate corresponding to the detection light of each wavelength, according to the target frequency domain signal of the fetus that corresponds to the detection light of each wavelength, comprises:

determining the fetal heart rate corresponding to the detection light of each wavelength, according to a signal obtained after sequentially performing frequency-time conversion processing, autocorrelation processing, and time-frequency conversion processing on the target frequency domain signal corresponding to the detection light of each wavelength.

For example, in the method for detecting fetal blood oxygen saturation provided in the at least one embodiment of this disclosure, the determining the corresponding fetal heart rate according to the preset rule, comprises:

selecting one wavelength of detection light in all types of the detection light, and determining the examined pregnant woman's heart rate according to the second photoplethysmography signals corresponding to the detection light; and determining the corresponding fetal heart rate, according to the examined pregnant woman's heart rate and a pre-stored correspondence table between pregnant women's heart rates and fetal heart rates.

For example, in the method for detecting fetal blood oxygen saturation provided in the at least one embodiment of this disclosure, the determining the target frequency domain signal of the fetus that corresponds to the detection light of each wavelength, according to the first photoplethysmography signals and the second photoplethysmography signals that correspond to the detection light of each wavelength, comprises:

respectively performing time-frequency conversion processing, with respect to the detection light of each wavelength, on the first photoplethysmography signals and the second photoplethysmography signals that correspond to the detection light, and determining a first frequency domain signal corresponding to the first photoplethysmography signals and a second frequency domain signal corresponding to the second photoplethysmography signals; and denoising, with respect to the detection light of each wavelength, the first frequency domain signal, by taking the second frequency domain signal as a noise signal of the first frequency domain signal, to obtain the target frequency domain signal corresponding to the detection light.

For example, in the method for detecting fetal blood oxygen saturation provided in the at least one embodiment of this disclosure, there are two wavelengths of the detection light; the determining the fetal blood oxygen saturation, according to the respective target photoplethysmography signals determined, comprises:

determining the fetal blood oxygen saturation SpO2 by using a formula below, according to the respective target photoplethysmography signals determined:

$$SpO_2 = \frac{\varepsilon_{RHb}^{\lambda_1}}{\varepsilon_{RHb}^{\lambda_1} - \varepsilon_{HbO_2}^{\lambda_1}} - \frac{\varepsilon_{RHb}^{\lambda_2}}{\varepsilon_{RHb}^{\lambda_1} - \varepsilon_{HbO_2}^{\lambda_1}} * \frac{R^{\lambda_1}}{R^{\lambda_2}};$$

$$R^{\lambda_1} = \frac{\Delta I^{\lambda_1}}{I_{min}^{\lambda_1}};$$

$$R^{\lambda_2} = \frac{\Delta I^{\lambda_2}}{I_{min}^{\lambda_2}},$$

wherein $\lambda 1$ represents a first wavelength in the two wavelengths; $\lambda 2$ represents a second wavelength in the two wavelengths; $\varepsilon_{RHb}^{\lambda_1}$ represents an absorption coefficient of reduced hemoglobin in a fetal artery that corresponds to detection light of the first wavelength; $\varepsilon_{RHb}^{\lambda_2}$ represents an absorption coefficient of reduced hemoglobin in the artery that corresponds to detection light of the second wavelength; $\varepsilon_{HbO_2}^{\lambda_1}$ represents an absorption coefficient of oxyhemoglobin in the artery that corresponds to the detection light of the first wavelength; $\Delta I^{\lambda_1}$ represents an amplitude value of a target photoplethysmography signal corresponding to the detection light of the first wavelength; $I_{min}^{\lambda_1}$ represents a minimum value of the target photoplethysmography signal corresponding to the detection light of the first wavelength; $\Delta I^{\lambda_2}$ represents an amplitude value of the target photoplethysmography signal corresponding to the detection light of the second wavelength; and $I_{min}^{\lambda_2}$ represents a minimum value of the target photoplethysmography signal corresponding to the detection light of the second wavelength.

At least one embodiment in this disclosure further provides an apparatus for detecting fetal blood oxygen saturation, comprising: a first detecting portion, a second detecting portion, and a signal processing portion;

the first detecting portion comprising: at least two first light sources and a first photoelectric volume detector, wherein each of the first light sources is configured to emit detection light of one wavelength, wavelengths of detection light emitted by the respective first light sources are different from each other, and the first photoelectric volume detector is configured to receive light of the detection light that is reflected by the fetus;

the second detecting portion comprising: at least two of the first light sources and a second photoelectric volume detector, wherein the second photoelectric volume detector is configured to receive light of the detection light that is transmitted through a detection site except an examined pregnant woman's abdomen;

the signal processing portion comprising: a first signal processing unit, a second signal processing unit, a third signal processing unit, and a blood oxygen saturation determining unit, wherein the first signal processing unit is configured to control the respective first light sources in the first detecting portion to emit detection light in a time-sharing manner, to irradiate the fetus in the examined pregnant woman's abdomen, and acquire first photoplethysmography signals corresponding to the abdomen under irradiation of the respective wavelength of detection light, according to light of the respective wavelength of detection light that is reflected by the fetus and received by the first photoelectric volume detector;

the second signal processing unit is configured to control the respective first light sources in the second detecting portion to emit detection light in a time-sharing manner, to irradiate the detection site; and acquire second photoplethysmography signals corresponding to the detection site under irradiation of the respective wavelength of detection light, according to light of the detection light that is transmitted through detection sites except the detection site and received by the second photoelectric volume detector;

the third signal processing unit is configured to determine a target photoplethysmography signal of the fetus that corresponds to the detection light of each wavelength, according to the first photoplethysmography signals and the second photoplethysmography signals that correspond to the detection light of each wavelength; and the blood oxygen saturation determining unit is configured to determine the fetal blood oxygen saturation, according to respective target photoplethysmography signals determined.

At least one embodiment in this disclosure further provides a computer-readable storage medium, having a computer program stored thereon, wherein the computer program, when executed by a processor, implements steps of the method in any items mentioned above for detecting fetal blood oxygen saturation.

At least one embodiment in this disclosure further provides a computer device, comprising a memory, a processor, and a computer program stored on the memory and executable on the processor, wherein the processor, when executing the computer program, implements steps of the method in any items mentioned above for detecting fetal blood oxygen saturation.

The embodiments of the present disclosure have advantageous effects below:

In the method and the apparatus for detecting fetal blood oxygen saturation provided by the embodiments of the present disclosure, at least two types of detection light of different wavelengths are used to irradiate a fetus in an examined pregnant woman's abdomen and acquire first photoplethysmography signals corresponding to the abdomen under irradiation of the respective wavelengths of detection light, in which way, when the detection light is used to irradiate the fetus of the examined pregnant woman's abdomen, the first photoplethysmography signals carrying both the examined pregnant woman's heart rate information and the fetal heart rate information may be obtained in a non-invasive manner. In addition, at least two types of detection light of different wavelengths are used to irradiate a detection site except the examined pregnant woman's abdomen in a time-sharing manner and acquire second photoplethysmography signals corresponding to the detection site under irradiation of the respective wavelengths of detection light, in which way, when the detection light is used to irradiate the examined pregnant woman's detection site, since the detection site is not the examined pregnant woman's abdomen, the second photoplethysmography signals carrying the examined pregnant woman's heart rate information may be obtained in a non-invasive manner; and thus, a target photoplethysmography signal of the fetus that corresponds to detection light of each wavelength may be determined according to a first photoplethysmography signals and a second photoplethysmography signals corresponding to detection light of each wavelength, that is, the target photoplethysmography signal is a photoplethysmography (PPG) signal carrying the fetal heart rate information after removing interference of the examined pregnant woman's heart rate information; and then fetal blood oxygen saturation may be determined according to the respective target photoplethysmography signals determined, so as to improve accuracy in detecting fetal blood oxygen saturation.

DETAILED DESCRIPTION

In order to make objects, technical details and advantages of the present disclosure apparent, the specific implementation modes of the method for detecting fetal blood oxygen saturation and the apparatus for detecting fetal blood oxygen saturation provided by the embodiments of the present disclosure will be described in details in connection with the drawings. It should be understood that, the embodiments described below only illustrate and explain the present disclosure, and are not intended to limit the present disclosure. In case of no conflict, the embodiments of the present disclosure and the features in the respective embodiments may be combined with each other. It should be noted that, shapes and sizes of respective patterns in the accompanying drawings do not reflect true proportions, but are only intended to illustrate contents of the present disclosure; and same or similar reference signs denote same or similar elements, or elements having same or similar functions from start to end.

A fetal pulse oximetry level in late pregnancy is an important physiological index to measure a fetal life state. Fetal pulse oximetry monitoring and adult pulse oximetry detection are on a same basic principle. Oxygen is a foundation for sustaining human life; systolic and diastolic functions of a heart make a human body's blood pulsate through lungs. A certain amount of reduced hemoglobin (HbR) combines with oxygen taken in the lungs to form oxyhemoglobin ($HbO_2$). The blood is transported through arteries all the way to capillaries, and then releases oxygen in the capillaries to maintain metabolism of tissue cells. Blood oxygen saturation ($SpO_2$) is a percentage of a volume of oxygen-combined oxyhemoglobin ($HbO_2$) to a total volume of combinable hemoglobin (Hb) in the blood, that is, a concentration of blood oxygen in the blood, which is an important physiological parameter of a respiratory cycle.

Figure 1:
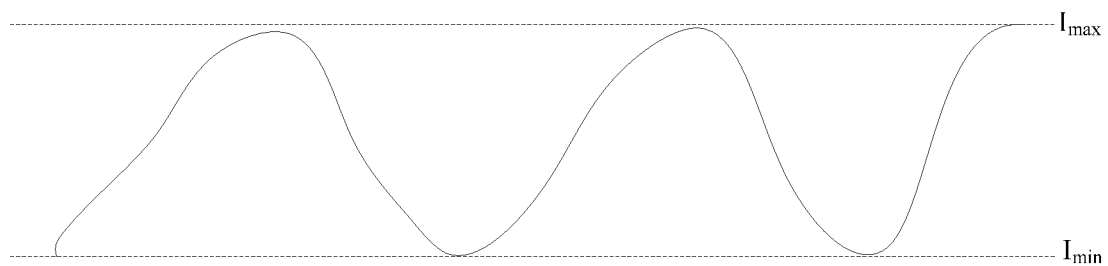
FIG. 1 is a signal schematic diagram of a photoplethysmography (PPG) signal.
Figure 2:
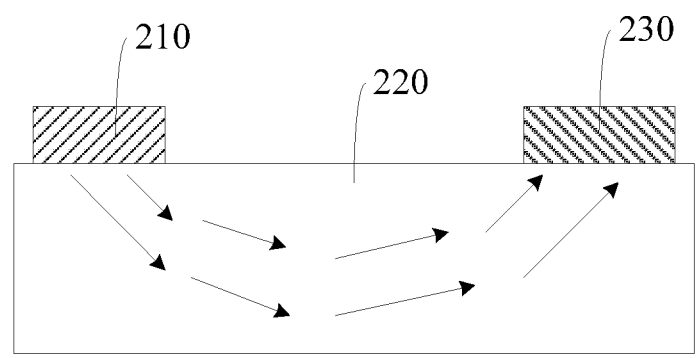
FIG. 2 is a schematic diagram of transmission and reception of the PPG signal.

During a pulsating cycle of the heart, blood flowing through arterioles, capillaries and venules in peripheral blood vessels shows a corresponding pulsatile change. A blood volume reaches maximum during systole, and the blood volume is minimum during diastole. In this way, photoplethysmography (PPG) may be used to acquire a tracing diagram of light absorption variation in the human tissue by using an optical technology, so as to acquire a PPG signal shown in FIG. 1. A working principle of PPG is that, as shown in FIG. 2, a light-emitting diode 210 irradiates light of a specific intensity and wavelength on an examined pregnant woman's skin surface layer 220, a photoelectric volume detector 230 detects an intensity of emergent light after passing through the skin surface layer 220, and depicts the PPG signal in an alternating current form shown in FIG. 1 according to the detected light intensity. The PPG signal is generated because the human heart delivers blood to respective tissues of the human body in each beat cycle, and blood vessels of the arteries and the arterioles of the skin surface layer 220 of the detection site periodically dilate and constrict due to pumping of the heart and blood perfusion. When systolic blood perfusion increases and the blood vessels dilate, absorbed light increases, and the signal received by the photoelectric volume detector 230 becomes weak; and conversely, the signal received by the photoelectric volume detector 230 becomes strong. This makes the PPG signal have a maximum value $I_{max}$ and a minimum value $I_{min}$.

That is, blood oxygen saturation may be detected in a non-traumatic manner on the principle that the amount of light absorbed by arterial blood varies with arterial pulses. Basic research shows that, oxyhemoglobin and deoxyhemoglobin have different absorption rates with respect to incident light of different wavelengths. When monochromatic light irradiates vertically on the human body, the amount of light absorbed by the arterial blood will vary with pulsation of arterial blood vessels in a light-transmitting region. In view of this, the embodiments of the present disclosure provide a method for detecting fetal blood oxygen saturation, in which fetal blood oxygen saturation is detected in a non-invasive manner, and accuracy of detected fetal blood oxygen saturation is improved.

Figure 3:
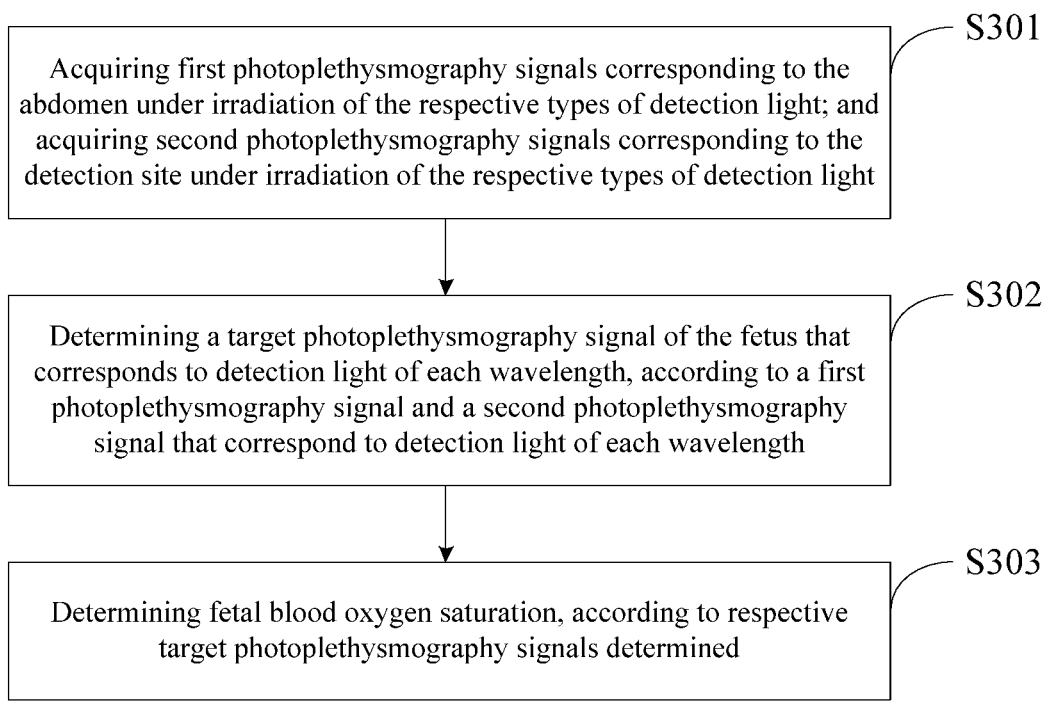
FIG. 3 is a flow chart of a method for detecting fetal blood oxygen saturation provided by an embodiment of the present disclosure.

As shown in FIG. 3, the method for detecting fetal blood oxygen saturation provided by the embodiment of the present disclosure comprises steps of:

S301: using at least two types of detection light of different wavelengths, to irradiate a fetus in an examined pregnant woman's abdomen in a time-sharing manner and acquiring first photoplethysmography signals (i.e., first PPG signals) corresponding to the abdomen under irradiation of the respective wavelengths of detection light; and to irradiate a detection site except the examined pregnant woman's abdomen in a time-sharing manner and acquiring second photoplethysmography signals (i.e., second PPG signals) corresponding to the detection site under irradiation of the respective wavelengths of detection light.

Since the detection site is a site of the examined pregnant woman except the abdomen, it is equivalent to that the second PPG signals carry only the examined pregnant woman's heart rate information. Further, in order to further reduce influence of a fetal heart rate on the second PPG signals, a site in the examined pregnant woman that is farther from the abdomen may be selected as the detection site, for example, a finger, an ankle or a toe may be used as the detection site. Hereinafter, description is provided by taking a finger as the detection site.

In general, a light-absorbing substance in blood under red and infrared light bands is hemoglobin, so two wavelengths of detection light may be set. Wherein, a first wavelength in the two wavelengths may be set to a wavelength of the red light band, which, for example, may be 660 nm; and in this way, a first PPG signal of the examined pregnant woman's abdomen under red light of 660 nm may be obtained, and a second PPG signal of the examined pregnant woman's finger under red light of 660 nm may be obtained. A second wavelength in the two wavelengths may be set to a wavelength of the infrared light band, which, for example, may be 940 nm; and in this way, a first PPG signal of the examined pregnant woman's abdomen under irradiation of infrared light of 940 nm may be obtained, and a second PPG signal of the examined pregnant woman's finger under irradiation of infrared light of 940 nm may be obtained. Of course, the first wavelength may also be, for example, 940 nm, and the second wavelength may also be, for example, 660 nm, which will not be limited here.

S302: determining a target photoplethysmography signal of the fetus that corresponds to detection light of each wavelength, according to a first photoplethysmography signals and a second photoplethysmography signals that correspond to detection light of each wavelength.

S303: determining fetal blood oxygen saturation, according to respective target photoplethysmography signals determined.

In the method for detecting fetal blood oxygen saturation provided by the embodiment of the present disclosure, at least two types of detection light of different wavelengths are used, to irradiate the fetus in the examined pregnant woman's abdomen in a time-sharing manner and the first photoplethysmography signals corresponding to the abdomen under irradiation of the respective wavelengths of detection light are acquired, in which way, when the detection light is used to irradiate the fetus of the examined pregnant woman's abdomen, the first photoplethysmography signals carrying both the examined pregnant woman's heart rate information and the fetal heart rate information may be obtained in a non-invasive manner. In addition, at least two wavelengths of detection light of different wavelengths are used to irradiate the detection site except the examined pregnant woman's abdomen in a time-sharing manner and the second photoplethysmography signals corresponding to the detection site under irradiation of the respective wavelengths of detection light are acquired, in which way, when the detection light is used to irradiate the examined pregnant woman's detection site, since the detection site is not the examined pregnant woman's abdomen, the second photoplethysmography signals carrying the examined pregnant woman's heart rate information may be obtained in a non-invasive manner. Thus, the target photoplethysmography signal of the fetus that corresponds to detection light of each wavelength may be determined according to a first photoplethysmography signals and a second photoplethysmography signals corresponding to detection light of each wavelength, that is, the target photoplethysmography signal is a photoplethysmography (PPG) signal carrying the fetal heart rate information after removing interference of the examined pregnant woman's heart rate information; and then fetal blood oxygen saturation may be determined according to the respective target photoplethysmography signals determined, so as to improve accuracy in detecting fetal blood oxygen saturation.

Hereinafter, the present disclosure will be described in detail in conjunction with specific embodiments. It should be noted that, the embodiments of the present disclosure are for better explanation of the present disclosure, but do not limit the present disclosure.

During actual implementation, in the embodiment of the present disclosure, the determining a target photoplethysmography signal of the fetus that corresponds to detection light of each wavelength, according to a first photoplethysmography signals and a second photoplethysmography signals that correspond to detection light of each wavelength, includes:

Determining a target frequency domain signal of the fetus that corresponds to each wavelength of detection light, according to the first photoplethysmography signals (i.e., the first PPG signal) and the second photoplethysmography signals (i.e., the second PPG signal) that correspond to each wavelength of detection light; and determining a corresponding fetal heart rate according to a preset rule;

Determining a target photoplethysmography signal (i.e., a target PPG signal) of the fetus that corresponds to each wavelength of detection light, according to the corresponding fetal heart rate determined and respective target frequency domain signals, so that the target PPG signal may be obtained according to the fetal heart rate.

During actual implementation, a target frequency domain signal of the fetus that corresponds to each wavelength of detection light may be determined according to a first PPG signal and a second PPG signal that correspond to each wavelength of detection light. For example, a target frequency domain signal of the fetus that corresponds to the detection light of the first wavelength is determined by the first PPG signal and the second PPG signal that correspond to the detection light of the first wavelength. A target frequency domain signal of the fetus that corresponds to the detection light of the second wavelength is determined by the first PPG signal and the second PPG signal that corresponds to the detection light of the second wavelength; and then, the corresponding fetal heart rate is determined according to the preset rule.

During actual implementation, in the embodiment of the present disclosure, the determining a target frequency domain signal of the fetus that corresponds to each wavelength of detection light, according to a first photoplethysmography signals and a second photoplethysmography signals that correspond to each wavelength of detection light, includes:

Respectively performing time-frequency conversion processing, with respect to each wavelength of detection light, on the first photoplethysmography signals and the second photoplethysmography signals that correspond to the detection light, and determining a first frequency domain signal corresponding to the first photoplethysmography signals and a second frequency domain signal corresponding to the second photoplethysmography signals;

Denoising, with respect to each wavelength of detection light, the first frequency domain signal, by taking the second frequency domain signal as a noise signal of the first frequency domain signal, to obtain the target frequency domain signal corresponding to the detection light, so that the obtained target frequency domain signal is a signal after removing the examined pregnant woman's heart rate information.

In the embodiment of the present disclosure, the determining a corresponding fetal heart rate according to a preset rule, includes: determining a fetal heart rate corresponding to each wavelength of detection light, according to a target frequency domain signal of the fetus that corresponds to each wavelength of detection light. Further, a fetal heart rate corresponding to each wavelength of detection light may be determined, according to a signal obtained after sequentially performing frequency-time conversion processing, autocorrelation processing, and time-frequency conversion processing on a target frequency domain signal corresponding to each wavelength of detection light. For example, frequency-time conversion processing, autocorrelation processing, and time-frequency conversion processing are performed on the target frequency domain signal of the fetus that corresponds to the detection light of the first wavelength, and the fetal heart rate corresponding to the detection light of the first wavelength is determined according to a signal subjected to the above-described frequency-time conversion processing, autocorrelation processing, and time-frequency conversion processing. Frequency-time conversion processing, autocorrelation processing, and time-frequency conversion processing are performed on the target frequency domain signal of the fetus that corresponds to the detection light of the second wavelength, and the fetal heart rate corresponding to the detection light of the second wavelength is determined according to a signal subjected to the above-described frequency-time conversion processing, autocorrelation processing, and time-frequency conversion processing.

For example, the determining a target photoplethysmography signal of the fetus that corresponds to each wavelength of detection light, according to the corresponding fetal heart rate determined and respective target frequency domain signals, includes: determining a target photoplethysmography signal of the fetus that corresponds to each wavelength of detection light, according to a fetal heart rate and the target frequency domain signal corresponding to each wavelength of detection light.

In general, the method for detecting blood oxygen saturation on the principle that the amount of light absorbed by arterial blood varies with arterial pulsation is based on absorbance A of blood. In conjunction with FIG. 2, a formula for absorbance A corresponding to detection light of a certain wavelength (with $\lambda_i$ as an example) satisfies:

$$A = \ln\frac{I_0^{\lambda_i}}{I^{\lambda_i}} = d\sum \varepsilon_m^{\lambda_i} C_m,$$

where, $I_0$ represents a light intensity of light emitted by the light-emitting diode 210; I represents a light intensity of light received by the photoelectric volume detector 230; d represents a path factor of light propagation; $1 \leq m \leq M$, and m is an integer; M represents a total number of light-absorbing substances; $\varepsilon_m$ represents an absorption coefficient of an m-th light-absorbing substance; and $C_m$ represents a concentration of the m-th light-absorbing substance.

Generally, an artery has a pulsating section and a stationary section, wherein, the pulsating section of the artery will affect a light intensity of incident light. Under irradiation of light of a specific light intensity at a certain wavelength (with $\lambda_i$ as an example), the photoelectric volume detector detects a PPG signal corresponding to $\lambda_i$, then an absorbance variation amount $\partial A^{\lambda_i}$ under arterial dilation and constriction may satisfy a formula:

$$\partial A^{\lambda_1} = A_{max}^{\lambda_1} - A_{min}^{\lambda_1} = \left(\varepsilon_{HbO_2}^{\lambda_1} C_{HbO_2} + \varepsilon_{RHb}^{\lambda_1} C_{RHb}\right) * \Delta L = -\ln\frac{I_{min}^{\lambda_1}}{I_{max}^{\lambda_1}} = \frac{\Delta I^{\lambda_1}}{I_{min}^{\lambda_1}};$$

wherein, $\Delta L$ represents a parameter; $A_{max}^{\lambda_i}$ represents maximum absorbance of the artery at the wavelength $\lambda_i$; $A_{min}^{\lambda_i}$ represents minimum absorbance of the artery at the wavelength $\lambda_i$; $\varepsilon_{HbO_2}^{\lambda_i}$ represents an absorption coefficient of oxyhemoglobin in the artery corresponding to light of the wavelength $\lambda_i$; $C_{HbO_2}$ represents a concentration of oxyhemoglobin in the artery; $\varepsilon_{RHb}^{\lambda_i}$ represents an absorption coefficient of reduced hemoglobin in the artery corresponding to light of the wavelength $\lambda_i$; and $C_{RHb}$ represents a concentration of reduced hemoglobin in the artery. $I_{min}^{\lambda_i}$ represents a minimum value of the PPG signal detected by the photoelectric volume detector at the wavelength $\lambda_i$; $I_{max}^{\lambda_i}$ represents a maximum value of the PPG signal detected by the photoelectric volume detector at the wavelength $\lambda_i$; and $\Delta I^{\lambda_i}$ represents an amplitude value between the maximum value and the minimum value of the PPG signal detected by the photoelectric volume detector at the wavelength $\lambda_i$.

During actual implementation, when there are two wavelengths of detection light, that is, the first wavelength and the second wavelength, an absorbance variation amount $\partial A^{\lambda_1}$ corresponding to the first wavelength (e.g., $\lambda_1$) may satisfy a formula:

$$\partial A^{\lambda_1} = A_{max}^{\lambda_1} - A_{min}^{\lambda_1} = \left(\varepsilon_{HbO_2}^{\lambda_1} C_{HbO_2} + \varepsilon_{RHb}^{\lambda_1} C_{RHb}\right) * \Delta L = -\ln\frac{I_{min}^{\lambda_1}}{I_{max}^{\lambda_1}} = \frac{\Delta I^{\lambda_1}}{I_{min}^{\lambda_1}}.$$

An absorbance variation amount $\partial A^{\lambda_2}$ corresponding to the second wavelength (e.g., $\lambda_2$) may satisfy a formula:

$$\partial A^{\lambda_1} = A_{max}^{\lambda_1} - A_{min}^{\lambda_1} = \left(\varepsilon_{HbO_2}^{\lambda_1} C_{HbO_2} + \varepsilon_{RHb}^{\lambda_1} C_{RHb}\right) * \Delta L = -\ln\frac{I_{min}^{\lambda_1}}{I_{max}^{\lambda_1}} = \frac{\Delta I^{\lambda_1}}{I_{min}^{\lambda_1}}.$$

Wherein, the second wavelength is an isoabsorptive point of oxyhemoglobin and reduced hemoglobin, that is, $\varepsilon_{HbO_2}^{\lambda_2} = \varepsilon_{RHb}^{\lambda_2}$, and by comparing $\partial A^{\lambda_1}$ with $\partial A^{\lambda_2}$, a formula that fetal blood oxygen saturation $SpO_2$ satisfies may be obtained:

$$SpO_2 = \frac{\varepsilon_{RHb}^{\lambda_1}}{\varepsilon_{RHb}^{\lambda_1} - \varepsilon_{HbO_2}^{\lambda_1}} - \frac{\varepsilon_{RHb}^{\lambda_2}}{\varepsilon_{RHb}^{\lambda_1} - \varepsilon_{HbO_2}^{\lambda_1}} * \frac{R^{\lambda_1}}{R^{\lambda_2}},$$

$$\text{wherein, } R^{\lambda_1} = \frac{\Delta I^{\lambda_1}}{I_{min}^{\lambda_1}}, R^{\lambda_2} = \frac{\Delta I^{\lambda_2}}{I_{min}^{\lambda_2}}.$$

During actual implementation, in the embodiment of the present disclosure, the determining fetal blood oxygen saturation, according to respective target photoplethysmography signals determined, includes: determining fetal blood oxygen saturation $SpO_2$ by using a formula below, according to the respective target photoplethysmography signals determined;

$$SpO_2 = \frac{\varepsilon_{RHb}^{\lambda_1}}{\varepsilon_{RHb}^{\lambda_1} - \varepsilon_{HbO_2}^{\lambda_1}} - \frac{\varepsilon_{RHb}^{\lambda_2}}{\varepsilon_{RHb}^{\lambda_1} - \varepsilon_{HbO_2}^{\lambda_1}} * \frac{R^{\lambda_1}}{R^{\lambda_2}};$$

$$R^{\lambda_1} = \frac{\Delta I^{\lambda_1}}{I_{min}^{\lambda_1}};$$

$$R^{\lambda_2} = \frac{\Delta I^{\lambda_2}}{I_{min}^{\lambda_2}},$$

where $\lambda_1$ represents the first wavelength in the two wavelengths; $\lambda_2$ represents the second wavelength in the two wavelengths; $\varepsilon_{RHb}^{\lambda_1}$ represents an absorption coefficient of the reduced hemoglobin in the fetal artery that corresponds to the detection light of the first wavelength; $\varepsilon_{RHb}^{\lambda_2}$ represents an absorption coefficient of the reduced hemoglobin in the artery that corresponds to the detection light of the second wavelength; $\varepsilon_{HbO_2}^{\lambda_1}$ represents an absorption coefficient of the oxyhemoglobin in the artery that corresponds to the detection light of the first wavelength; $\Delta I^{\lambda_1}$ represents an amplitude value of the target photoplethysmography signal corresponding to the detection light of the first wavelength; $I_{min}^{\lambda_1}$ represents a minimum value of the target photoplethysmography signal corresponding to the detection light of the first wavelength; $\Delta I^{\lambda_2}$ represents an amplitude value between a maximum value and a minimum value of the target photoplethysmography signal corresponding to the detection light of the second wavelength; and $I_{min}^{\lambda_2}$ represents a minimum value of the target photoplethysmography signal corresponding to the detection light of the second wavelength.

Hereinafter, the detecting method provided by the present disclosure will be described in detail through a specific embodiment.

The method for detecting fetal blood oxygen saturation provided by the embodiment of the present disclosure may comprise steps of:

(1) Using the detection light of the first wavelength $\lambda_1$ to irradiate the fetus in the examined pregnant woman's abdomen, and acquiring a first PPG signal S1_1 corresponding to the abdomen under irradiation of the detection light of the first wavelength $\lambda_1$. The first PPG signal S1_1 carries both the examined pregnant woman's heart rate information and the fetal heart rate information.

(2) Using the detection light of the second wavelength $\lambda_2$ to irradiate the fetus in the examined pregnant woman's abdomen, and acquiring a first PPG signal S1_2 corresponding to the abdomen under irradiation of the detection light of the second wavelength $\lambda_2$. The first PPG signal S1_2 carries both the examined pregnant woman's heart rate information and the fetal heart rate information.

(3) Using the detection light of the first wavelength $\lambda_1$ to irradiate the detection site, and acquiring a second PPG signal S2_1 corresponding to the detection site under irradiation of the detection light of the first wavelength $\lambda_1$, so that the second PPG signal S2_1 only carries the examined pregnant woman's heart rate information.

(4) Using the detection light of the second wavelength $\lambda_2$ to irradiate the detection site, and acquiring a second PPG signal S2_2 corresponding to the detection site under irradiation of the detection light of the second wavelength $\lambda_2$, so that the second PPG signal S2_2 only carries the examined pregnant woman's heart rate information.

(5) Generally the PPG signal obtained by detection being a time domain signal, then performing time-frequency conversion processing (e.g., Fast Fourier Transformation (FFT)) on the first PPG signal S1_1 corresponding to the detection light of the first wavelength $\lambda_1$, to convert the first PPG signal S1_1 in a form of a time domain signal into a signal in a form of a frequency domain signal, that is, a first frequency domain signal P1_1. Similarly, time-frequency conversion processing is performed on the first PPG signal S1_2 corresponding to the detection light of the second wavelength $\lambda_2$, to convert the first PPG signal S1_2 in the form of the time domain signal into a signal in the form of the frequency domain signal, that is, a first frequency domain signal P1_2.

Time-frequency conversion processing is performed on the second PPG signal S2_1 corresponding to the detection light of the first wavelength $\lambda_1$, to convert the second PPG signal S2_1 in the form of the time domain signal into a signal in the form of the frequency domain signal, that is, a second frequency domain signal P2_1. Similarly, time-frequency conversion processing is performed on the second PPG signal S2_2 corresponding to the detection light of the second wavelength $\lambda_2$, to convert the second PPG signal S2_2 in the form of the time domain signal into a signal in the form of the frequency domain signal, that is, a second frequency domain signal P2_2.

(6) Denoising, with respect to the detection light of the first wavelength $\lambda_1$, the first frequency domain signal P1_1, by taking the second frequency domain signal P2_1 as a noise signal of the first frequency domain signal P1_1, to obtain a target frequency domain signal M0_1 corresponding to the detection light of the first wavelength $\lambda_1$. In this way, the examined pregnant woman's heart rate information carried in the first frequency domain signal P1_1 may be removed, so that the target frequency domain signal M0_1 may be understood as the fetal heart rate as well as its frequency multiplication and background interference.

Similarly, with respect to the detection light of the second wavelength $\lambda_2$, the first frequency domain signal P1_2 is denoised, by taking the second frequency domain signal P2_2 as a noise signal of the first frequency domain signal P1_2, to obtain a target frequency domain signal M0_2 corresponding to the detection light of the second wavelength $\lambda_2$. In this way, the examined pregnant woman's heart rate information carried in the first frequency domain signal P1_2 may be removed, so that the target frequency domain signal M0_2 may be understood as the fetal heart rate as well as its frequency multiplication and background interference.

(7) Performing frequency-time conversion processing on the target frequency domain signal M0_1 with respect to the detection light of the first wavelength $\lambda_1$ to convert the target frequency domain signal M0_1 into the target time domain signal MS0_1; then performing autocorrelation processing on the target time domain signal MS0_1, to further highlight periodicity of the signal, that is, a fetal heartbeat cycle, while suppressing an effect of a random noise or an artifact on signal quality. Next, time-frequency conversion processing is performed on the signal subjected to autocorrelation processing to obtain a target frequency domain signal M0_1' in the form of the frequency domain signal. Thereafter, the fetal heart rate corresponding to the detection light of the first wavelength $\lambda_1$ may be determined by screening a peak point according to the target frequency domain signal M0_1'.

Similarly, frequency-time conversion processing is performed on the target frequency domain signal M0_2 with respect to the detection light of the second wavelength $\lambda_2$ to convert the target frequency domain signal M0_2 into the target time domain signal MS0_2; and then autocorrelation processing is performed on the target time domain signal MS0_2, to further highlight periodicity of the signal, that is, the fetal heartbeat cycle, while suppressing an effect of a random noise or an artifact on signal quality. Next, time-frequency conversion processing is performed on the signal subjected to autocorrelation processing to obtain a target frequency domain signal M0_2' in the form of the frequency domain signal. Thereafter, the fetal heart rate corresponding to the detection light of the second wavelength $\lambda_2$ may be determined by screening a peak point according to the target frequency domain signal M0_2'.

(8) Selecting a value in the target frequency domain signal M0_1 that corresponds to the heart rate according to the corresponding fetal heart rate with respect to the detection light of the first wavelength $\lambda_1$, to depict a target PPG signal S3_1 corresponding to the fetus. Of course, a maximum value, a minimum value, and an amplitude value of the corresponding heart rate may also be selected in the target frequency domain signal M0_1 according to the corresponding fetal heart rate, to determine the target PPG signal S3_1, which will not be limited here.

Similarly, a value corresponding to the heart rate is selected in the target frequency domain signal M0_2 according to the corresponding fetal heart rate with respect to the detection light of the second wavelength $\lambda_2$, to depict a target PPG signal S3_2 corresponding to the fetus. Of course, a maximum value, a minimum value, and an amplitude value of the corresponding heart rate may also be selected in the target frequency domain signal M0_2 according to the corresponding fetal heart rate, to determine the target PPG signal S3_2, which will not be limited here.

(9) Determining fetal blood oxygen saturation SpO$_2$ by using a formula below according to the target PPG signal S3_1 and the target PPG signal S3_2 determined;

$$SpO_2 = \frac{\varepsilon_{RHb}^{\lambda_1}}{\varepsilon_{RHb}^{\lambda_1} - \varepsilon_{HbO_2}^{\lambda_1}} - \frac{\varepsilon_{RHb}^{\lambda_2}}{\varepsilon_{RHb}^{\lambda_1} - \varepsilon_{HbO_2}^{\lambda_1}} * \frac{R^{\lambda_1}}{R^{\lambda_2}};$$

$$R^{\lambda_1} = \frac{\Delta I^{\lambda_1}}{I_{min}^{\lambda_1}};$$

$$R^{\lambda_2} = \frac{\Delta I^{\lambda_2}}{I_{min}^{\lambda_2}}.$$

It should be noted that, in the above-described embodiment, the description is only in an order of steps (1) to (4); in actual application, step (1) and step (3) may be performed simultaneously, and step (2) and step (4) may be performed simultaneously; or step (1) and step (4) may be performed simultaneously, and step (2) and step (3) may be performed simultaneously, which may be designed and determined according to an actual application environment and will not be limited here.

An embodiment of the present disclosure modifies the above-described implementation mode of determining the corresponding fetal heart rate according to a preset rule. Hereinafter, only differences from the above-described embodiment will be described, and similarities will not be repeated here.

During actual implementation, in the embodiment of the present disclosure, the determining the corresponding fetal heart rate according to a preset rule, may include:

Selecting one wavelength of detection light in all wavelengths of detection light, and determining the examined pregnant woman's heart rate according to the second photoplethysmography signals corresponding to the detection light;

Determining the corresponding fetal heart rate according to the examined pregnant woman's heart rate and a pre-stored correspondence table between pregnant women's heart rates and fetal heart rates.

Generally, there is a mapping relationship between fetal heart rates and pregnant women's heart rates; and during actual implementation, in the embodiment of the present disclosure, the method for determining the pre-stored correspondence table between pregnant women's heart rates and fetal heart rates, may include:

Acquiring heart rates of a plurality of pre-selected pregnant women, and using a fetal heart monitor to acquire fetal heart rates of the respective pre-selected pregnant women;

Determining the correspondence table between the pregnant women's heart rates and the fetal heart rates, according to the heart rates of the respective pre-selected pregnant women and the fetal heart rates of the respective pre-selected pregnant women acquired. Wherein, the correspondence table between the pregnant women's heart rates and the fetal heart rates includes: the heart rates of the plurality of pregnant women and the fetal heart rates in one-to-one correspondence with each pregnant woman's heart rates.

Hereinafter, the detecting method provided by the embodiment of the present disclosure will be described in detail through a specific embodiment.

The method for detecting fetal blood oxygen saturation provided by the embodiment of the present disclosure may comprise steps of:

(1) Using the detection light of the first wavelength $\lambda_1$ to irradiate the fetus in the examined pregnant woman's abdomen, and acquiring a first PPG signal S1_1 corresponding to the abdomen under irradiation of the detection light of the first wavelength $\lambda_1$. The first PPG signal S1_1 carries both the examined pregnant woman's heart rate information and the fetal heart rate information.

(2) Using the detection light of the second wavelength $\lambda_2$ to irradiate the fetus in the examined pregnant woman's abdomen, and acquiring a first PPG signal S1_2 corresponding to the abdomen under irradiation of the detection light of the second wavelength $\lambda_2$. The first PPG signal S1_2 carries both the examined pregnant woman's heart rate information and the fetal heart rate information.

(3) Using the detection light of the first wavelength $\lambda_1$ to irradiate the detection site, and acquiring a second PPG signal S2_1 corresponding to the detection site under irradiation of the detection light of the first wavelength $\lambda_1$, so that the second PPG signal S2_1 only carries the examined pregnant woman's heart rate information.

(4) Using the detection light of the second wavelength $\lambda_2$ to irradiate the detection site, and acquiring a second PPG signal S2_2 corresponding to the detection site under irradiation of the detection light of the second wavelength $\lambda_2$, so that the second PPG signal S2_2 only carries the examined pregnant woman's heart rate information.

(5) Generally the PPG signal obtained by detection being a time domain signal, then performing time-frequency conversion processing (e.g., Fast Fourier Transformation (FFT)) on the first PPG signal S1_1 corresponding to the detection light of the first wavelength $\lambda_1$, to convert the first PPG signal S1_1 in a form of a time domain signal into a signal in a form of a frequency domain signal, that is, a first frequency domain signal P1_1. Similarly, time-frequency conversion processing is performed on the first PPG signal S1_2 corresponding to the detection light of the second wavelength $\lambda_2$, to convert the first PPG signal S1_2 in the form of the time domain signal into a signal in the form of the frequency domain signal, that is, a first frequency domain signal P1_2.

Time-frequency conversion processing is performed on the second PPG signal S2_1 corresponding to the detection light of the first wavelength $\lambda_1$, to convert the second PPG signal S2_1 in the form of the time domain signal into a signal in the form of the frequency domain signal, that is, a second frequency domain signal P2_1. Similarly, time-frequency conversion processing is performed on the second PPG signal S2_2 corresponding to the detection light of the second wavelength $\lambda_2$, to convert the second PPG signal S2_2 in the form of the time domain signal into a signal in the form of the frequency domain signal, that is, a second frequency domain signal P2_2.

(6) Denoising, with respect to the detection light of the first wavelength $\lambda_1$, the first frequency domain signal P1_1, by taking the second frequency domain signal P2_1 as a noise signal of the first frequency domain signal P1_1, to obtain a target frequency domain signal M0_1 corresponding to the detection light of the first wavelength $\lambda_1$. In this way, the examined pregnant woman's heart rate information carried in the first frequency domain signal P1_1 may be removed, so that the target frequency domain signal M0_1 may be understood as the fetal heart rate as well as its frequency multiplication and background interference.

Similarly, with respect to the detection light of the second wavelength $\lambda_2$, the first frequency domain signal P1_2 is denoised, by taking the second frequency domain signal P2_2 as a noise signal of the first frequency domain signal P1_2, to obtain a target frequency domain signal M0_2 corresponding to the detection light of the second wavelength $\lambda_2$. In this way, the examined pregnant woman's heart rate information carried in the first frequency domain signal P1_2 may be removed, so that the target frequency domain signal M0_2 may be understood as the fetal heart rate as well as its frequency multiplication and background interference.

(7) Selecting the detection light of the first wavelength, and determining the examined pregnant woman's heart rate according to the second PPG signal S2_1 corresponding to the detection light. Of course, the detection light of the second wavelength may also be selected to determine the examined pregnant woman's heart rate according to the second PPG signal S2_2 corresponding to the detection light.

Thereafter, the corresponding fetal heart rate may be determined according to the examined pregnant woman's heart rate determined and the pre-stored correspondence table between the pregnant women's heart rates and the fetal heart rates.

(8) Selecting a value in the target frequency domain signal M0_1 that corresponds to the heart rate according to the corresponding fetal heart rate with respect to the detection light of the first wavelength $\lambda_1$, to depict a target PPG signal S3_1 corresponding to the fetus. Of course, a maximum value, a minimum value, and an amplitude value of the corresponding heart rate may also be selected in the target frequency domain signal M0_1 according to the corresponding fetal heart rate, to determine the target PPG signal S3_1, which will not be limited here.

Similarly, a value corresponding to the heart rate is selected in the target frequency domain signal M0_2 according to the corresponding fetal heart rate with respect to the detection light of the second wavelength $\lambda_2$, to depict a target PPG signal S3_2 corresponding to the fetus. Of course, a maximum value, a minimum value, and an amplitude value of the corresponding heart rate may also be selected in the target frequency domain signal M0_2 according to the corresponding fetal heart rate, to determine the target PPG signal S3_2, which will not be limited here.

(9) Determining fetal blood oxygen saturation $SpO_2$ by using a formula below according to the target PPG signal S3_1 and the target PPG signal S3_2 determined;

$$SpO_2 = \frac{\varepsilon_{RHb}^{\lambda_1}}{\varepsilon_{RHb}^{\lambda_1} - \varepsilon_{HbO_2}^{\lambda_1}} - \frac{\varepsilon_{RHb}^{\lambda_2}}{\varepsilon_{RHb}^{\lambda_1} - \varepsilon_{HbO_2}^{\lambda_1}} * \frac{R^{\lambda_1}}{R^{\lambda_2}};$$

$$R^{\lambda_1} = \frac{\Delta I^{\lambda_1}}{I_{min}^{\lambda_1}};$$

$$R^{\lambda_2} = \frac{\Delta I^{\lambda_2}}{I_{min}^{\lambda_2}}.$$

It should be noted that, in the above-described embodiment, the description is only in an order of steps (1) to (4); in actual application, step (1) and step (3) may be performed simultaneously, and step (2) and step (4) may be performed simultaneously; or step (1) and step (4) may be performed simultaneously, and step (2) and step (3) may be performed simultaneously, which may be designed and determined according to an actual application environment and will not be limited here.

It should be noted that, in the above-described embodiment, the description is only in an order of steps (5) to (7); in actual application, step (7) may also be made before step (5) and step (6), which may be designed and determined according to an actual application environment and will not be limited here.

Figure 4:
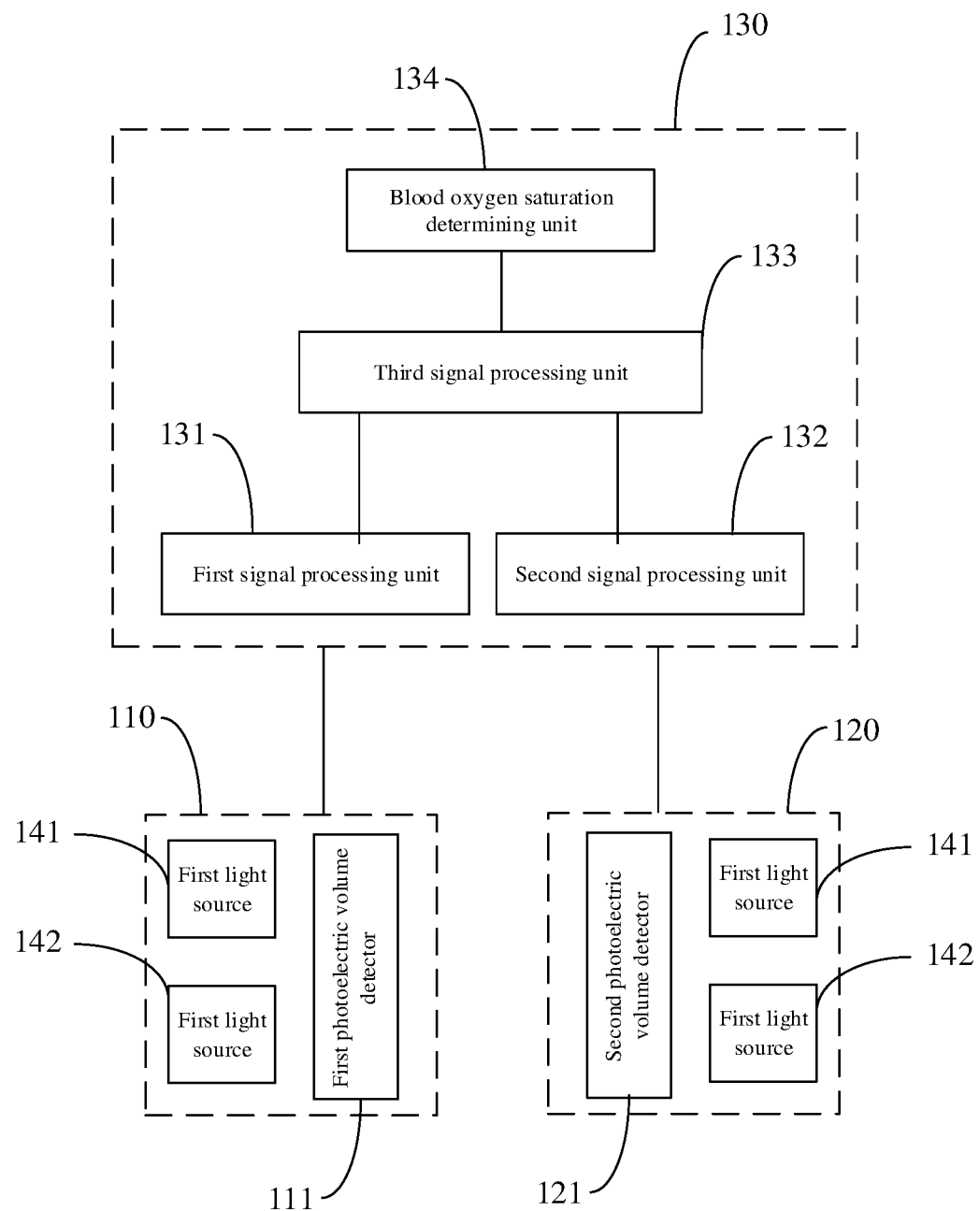
FIG. 4 is a structural schematic diagram of an apparatus for detecting fetal blood oxygen saturation provided by an embodiment of the present disclosure.

Based on a same inventive concept, an embodiment of the present disclosure further provides an apparatus for detecting fetal blood oxygen saturation; and as shown in FIG. 4, the apparatus for detecting fetal blood oxygen saturation comprises: a first detecting portion 110, a second detecting portion 120 and a signal processing portion 130; wherein, the first detecting portion 110 includes: at least two first light sources (with two first light sources 141 and 142 as an example in FIG. 4) and a first photoelectric volume detector 111; each first light source is configured to emit detection light of one wavelength, wavelengths of detection light emitted by the respective first light sources being different from each other; the first photoelectric volume detector 111 is configured to receive light of the detection light that is reflected back by a fetus; the first light source 141 may be a light-emitting diode that emits detection light of a first wavelength, and the first light source 142 may be a light-emitting diode that emits detection light of a second wavelength.

The second detecting portion 120 includes: at least two first light sources (with two first light sources 141 and 142 as an example in FIG. 4) and a second photoelectric volume detector 121; the second photoelectric volume detector is configured to receive light of the detection light that is transmitted through a detection site except an examined pregnant woman's abdomen.

The signal processing portion 130 includes: a first signal processing unit 131, a second signal processing unit 132, a third signal processing unit 133, and a blood oxygen saturation determining unit 134; wherein, the first signal processing unit 131 is configured to control the respective first light sources in the first detecting portion 110 to emit detection light in a time-sharing manner, to irradiate the fetus in the examined pregnant woman's abdomen; and acquire first photoplethysmography signals (i.e., first PPG signals) corresponding the abdomen under irradiation of the respective wavelengths of detection light, according to light of the respective wavelengths of detection light that is reflected back from the fetus and received by the first photoelectric volume detector 111.

The second signal processing unit 132 is configured to control the respective first light sources in the second detecting portion 120 to emit detection light in a time-sharing manner, to irradiate the detection site; and acquire second photoplethysmography signals (i.e., second PPG signals) corresponding to the detection site under irradiation of the respective types of detection light, according to light of the detection light that is transmitted through the detection site and received by the second photoelectric volume detector 121;

The third signal processing unit 133 is configured to determine a target photoplethysmography signal of the fetus that corresponds to detection light of each wavelength, according to first photoplethysmography signals and second photoplethysmography signals that correspond to detection light of each wavelength;

The blood oxygen saturation determining unit 134 is configured to determine fetal blood oxygen saturation, according to the respective target photoplethysmography signals determined.

During actual implementation, in the embodiment of the present disclosure, the above-described respective units may take a form of an embodiment combining software and hardware.

During actual implementation, in the embodiment of the present disclosure, the above-described respective units may implement the steps of any one of the above-described methods for detecting fetal blood oxygen saturation provided by the embodiments of the present disclosure, and no details will be specifically repeated here.

In addition, the principle on which the apparatus for detecting fetal blood oxygen saturation solves the problem is similar to that of the foregoing method for detecting fetal blood oxygen saturation, so the implementation of the foregoing method for detecting fetal blood oxygen saturation may be referred to for implementation of the apparatus for detecting fetal blood oxygen saturation, and no details will be repeated here.

During actual implementation, in the embodiment of the present disclosure, the first signal processing unit may be provided in the first detecting portion, and of course, may also be provided outside the first detecting portion, which will not be limited here.

During actual implementation, in the embodiment of the present disclosure, the second signal processing unit may be provided in the second detecting portion, and of course, may also be provided outside the second detecting portion, which will not be limited here.

Figure 5:
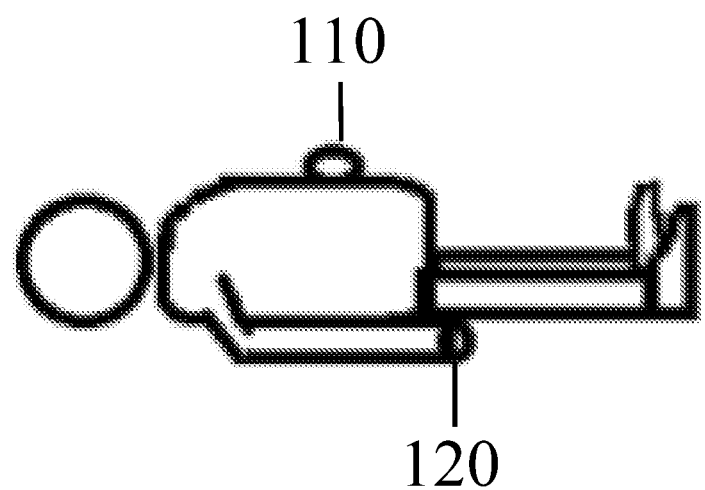
FIG. 5 is a schematic diagram of placement of the apparatus for detecting during detection provided by an embodiment of the present disclosure.

During actual implementation, in the embodiment of the present disclosure, as shown in FIG. 5, when detecting fetal blood oxygen saturation, the first detecting portion 110 may be provided outside the examined pregnant woman's body, that is, on the abdomen.

During actual implementation, in the embodiment of the present disclosure, as shown in FIG. 5, when detecting fetal blood oxygen saturation, the second detecting portion 120 may be provided outside the examined pregnant woman's detection site, that is, on a finger.

Based on a same inventive concept, an embodiment of the present disclosure further provides a computer-readable storage medium, having a computer program stored thereon, wherein, the computer program, when executed by a processor, implements the steps of any one of the above-described methods for detecting fetal blood oxygen saturation provided by the embodiments of the present disclosure. Specifically, the embodiments of the present disclosure may adopt the form of computer program product which is implemented on one or more computer usable storage mediums (including, but not limited to, a disk storage, and an optical storage, etc.) with computer usable program codes stored thereon.

Based on a same inventive concept, an embodiment of the present disclosure further provides a computer device, comprising a memory, a processor, and a computer program stored on the memory and executable on the processor, wherein, the processor, when executing the computer program, implements the steps of any one of the above-described methods for detecting fetal blood oxygen saturation provided by the embodiments of the present disclosure.

In the method and the apparatus for detecting fetal blood oxygen saturation, the computer-readable storage medium and the computer device provided by the embodiments of the present disclosure, at least two types of detection light of different wavelengths are used to irradiate the fetus in the examined pregnant woman's abdomen and the first photoplethysmography signals corresponding to the abdomen under irradiation of the respective types of detection light are acquired, in which way, when the detection light is used to irradiate the fetus of the examined pregnant woman's abdomen, the first photoplethysmography signals carrying both the examined pregnant woman's heart rate information and the fetal heart rate information may be obtained in a non-invasive manner. In addition, at least two types of detection light of different wavelengths are used to irradiate the detection site except the examined pregnant woman's abdomen in a time-sharing manner and the second photoplethysmography signals corresponding to the detection site under irradiation of the respective types of detection light are acquired, in which way, when the detection light is used to irradiate the examined pregnant woman's detection site, since the detection site is not the examined pregnant woman's abdomen, the second photoplethysmography signals carrying the examined pregnant woman's heart rate information may be obtained in a non-invasive manner. Thus, a target photoplethysmography signal of the fetus that corresponds to detection light of each wavelength may be determined according to a first photoplethysmography signals and a second photoplethysmography signals that correspond to detection light of each wavelength, that is, the target photoplethysmography signal is a PPG signal carrying the fetal heart rate information after removing interference of the examined pregnant woman's heart rate information. Then, fetal blood oxygen saturation may be determined according to the respective target photoplethysmography signals determined, so as to improve accuracy in detecting fetal blood oxygen saturation.

It is evident that one person skilled in the art can make various changes or modifications to the embodiments of the present disclosure without departure from the spirit and scope of the present disclosure. Thus, if these changes and modifications to the embodiments of the present disclosure are within the scope of the claims of the present disclosure and equivalent technologies, the present disclosure also intends to include all such changes and modifications within its scope.

The invention claimed is:

1. A method for detecting fetal blood oxygen saturation, comprising:

using at least two detection light of different wavelengths to irradiate a fetus in an examined pregnant woman's abdomen in a time-sharing manner and acquiring first photoplethysmography signals corresponding to the abdomen under irradiation of the respective wavelengths of detection light, and to irradiate a detection site except the examined pregnant woman's abdomen in a time-sharing manner and acquiring second photoplethysmography signals corresponding to the detection site under irradiation of the respective wavelengths of the detection light;

determining a target photoplethysmography signal of the fetus that corresponds to the detection light of each wavelength, according to the first photoplethysmography signals and the second photoplethysmography signals that correspond to the detection light of each wavelength; and determining the fetal blood oxygen saturation, according to respective target photoplethysmography signals determined, wherein the determined the target photoplethysmography signal of the fetus that corresponds to the detection light of each wavelength, according to the first photoplethysmography signals and the second photoplethysmography signals that correspond to the detection light of each wavelength, comprises:

determine a target frequency domain signal of the fetus that corresponds to the detection light of each wavelength, according to the first photoplethysmography signals and the second photoplethysmography signals that correspond to each wavelength of that detection light;

determining a corresponding fetal heart rate according to a preset rule; and determining the target photoplethysmography signal of the fetus that corresponds to the detection light of each wavelength, according to the corresponding fetal heart rate determined and respective target frequency domain signals, wherein the determining the corresponding fetal heart rate according to the present rule comprises;

determining a fetal heart rate corresponding to each wavelength of the detection light, according to the target frequency domain signal of the fetus that corresponds to each wavelength of the detection light, wherein the determining the target photoplethsmography signal of the fetus that corresponds to the detection light of each wavelength, according to the corresponding fetal heart rate determined and the respective target frequency domain signals, comprises:

determining the target photoplethysmography signal of the fetus that corresponds to the detection light of each wavelength, according to the fetal heart rate and the target frequency domain signal corresponding to the detection light of each wavelength, and wherein the determining the fetal heart rate corresponding to each wavelength of the detection light, according to the target frequency domain signal of the fetus that corresponds to each wavelength of the detection light, comprises:

determining the fetal heart rate corresponding to the detection light of each wavelength, according to a signal obtained after sequentially performing frequency-time conversion processing, autocorrelation processing, and time-frequency conversion processing on the target frequency domain signal corresponding to the detection light of each wavelength.

2. The method for detecting fetal blood oxygen saturation according to claim 1, wherein the determining the target frequency domain signal of the fetus that corresponds to each wavelength of the detection light, according to the first photoplethysmography signals and the second photoplethysmography signals that correspond to each wavelength of the detection light, comprises:

respectively performing time-frequency conversion processing, with respect to the detection light of each wavelength, on the first photoplethysmography signals and the second photoplethysmography signals that correspond to the detection light of each wavelength, and determining a first frequency domain signal corresponding to the first photoplethysmography signals and a second frequency domain signal corresponding to the second photoplethysmography signals; and denoising, with respect to the detection light of each wavelength, the first frequency domain signal, by taking the second frequency domain signal as a noise signal of the first frequency domain signal, to obtain the target frequency domain signal corresponding to the detection light of each wavelength.

3. The method for detecting fetal blood oxygen saturation according to claim 1, wherein there are two wavelengths of the detection light; the determining the fetal blood oxygen saturation, according to the respective target photoplethysmography signals determined, comprises:

determining the fetal blood oxygen saturation $SpO_2$ by using a formula below, according to the respective target photoplethysmography signals determined:

$$SpO_2 = \frac{\varepsilon_{RHb}^{\lambda_1}}{\varepsilon_{RHb}^{\lambda_1} - \varepsilon_{HbO_2}^{\lambda_1}} - \frac{\varepsilon_{RHb}^{\lambda_2}}{\varepsilon_{RHb}^{\lambda_1} - \varepsilon_{HbO_2}^{\lambda_1}} * \frac{R^{\lambda_1}}{R^{\lambda_2}};$$

$$R^{\lambda_1} = \frac{\Delta I^{\lambda_1}}{I_{min}^{\lambda_1}};$$

$$R^{\lambda_2} = \frac{\Delta I^{\lambda_2}}{I_{min}^{\lambda_2}},$$

wherein $\lambda_1$ represents a first wavelength in the two wavelengths; $\lambda_2$ represents a second wavelength in the two wavelengths; $\varepsilon_{RHb}^{\lambda_1}$ represents an absorption coefficient of reduced hemoglobin in a fetal artery that corresponds to detection light of the first wavelength; $\varepsilon_{RHb}^{\lambda_2}$ represents an absorption coefficient of reduced hemoglobin in the fetal artery that corresponds to detection light of the second wavelength; $\varepsilon_{HbO_2}^{\lambda_1}$ represents an absorption coefficient of oxyhemoglobin in the fetal artery that corresponds to the detection light of the first wavelength; $\Delta I^{\lambda_1}$ represents an amplitude value of a target photoplethysmography signal corresponding to the detection light of the first wavelength; $I_{min}^{\lambda_1}$ represents a minimum value of the target photoplethysmography signal corresponding to the detection light of the first wavelength; $\Delta I^{\lambda_2}$ represents an amplitude value of the target photoplethysmography signal corresponding to the detection light of the second wavelength; and $I_{min}^{\lambda_2}$ represents a minimum value of the target photoplethysmography signal corresponding to the detection light of the second wavelength.

4. A non-transitory computer-readable storage medium, having a computer program stored thereon, wherein the computer program, when executed by a processor, implements the method for detecting fetal blood oxygen saturation according to claim 1.

5. A computer device, comprising a memory, a processor, and a computer program stored on the memory and executable by the processor, wherein the processor, when executing the computer program, implements the method for detecting fetal blood oxygen saturation according to claim 1.

6. A method for detecting fetal blood oxygen saturation, comprising:
using at least two detection light of different wavelengths to irradiate a fetus in an examined pregnant woman's abdomen in a time-sharing manner and acquiring first photoplethysmography signals corresponding to the abdomen under irradiation of the respective wavelengths of detection light, and to irradiate a detection site except for the examined pregnant women's abdomen in a time-sharing manner and acquire second photoplethsymography signals to corresponding to the detection site under irradiation of the respective wavelengths of the detection light;
determining a target photoplethysmography signal of the fetus that corresponds to detection light of each wavelength, according to the first photoplethysmography signals and the second photoplethysmography signals that correspond to the detection light each wavelength, and
determining the fetal blood oxygen saturation, according to respective target photoplethysmography signals determined,
wherein the determining the target photoplethysmography signal of the fetus that corresponds to the detection light of each wavelength, according to the first photoplethysmography signals and the second photoplethysmography signals that correspond to the detection light of each wavelength, comprises:
determining a target frequency domain signal of the fetus that corresponds to the detection light of each wavelength, according to the first photoplethysmography signals and the second photoplethysmography signals that correspond to each wavelength of the detection light;
determining a corresponding fetal heart rate according to a present rule; and
determining the target photoplethysmography signal of the fetus that corresponds to the detection light of each wavelength, according to the corresponding fetal heart rate determined and respective target frequency domain signals,
wherein the determining the corresponding fetal heart rate according to the preset rule comprises:
selecting one wavelength of detection light in all wavelengths of the detection light, and determining the examined pregnant woman's heart rate according to second photoplethysmography signals corresponding to the selected one wavelength of detection light; and
determining the corresponding fetal heart rate, according to the examined pregnant woman's heart rate and a pre-stored correspondence table between pregnant women's heart rates and fetal heart rates.

7. The method for detecting fetal blood oxygen saturation according to claim 6, wherein the determining the target frequency domain signal of the fetus that corresponds to each wavelength of the detection light, according to the first photoplethysmography signals and the second photoplethysmography signals that correspond to each wavelength of the detection light, comprises:
respectively performing time-frequency conversion processing, with respect to the detection light of each wavelength, on the first photoplethysmography signals and the second photoplethysmography signals that correspond to the detection light of each wavelength, and determining a first frequency domain signal corresponding to the first photoplethysmography signals and a second frequency domain signal corresponding to the second photoplethysmography signals; and
denoising, with respect to the detection light of each wavelength, the first frequency domain signal, by taking the second frequency domain signal as a noise signal of the first frequency domain signal, to obtain the target frequency domain signal corresponding to the detection light of each wavelength.

8. The method for detecting fetal blood oxygen saturation according to claim 6, wherein there are two wavelengths of the detection light; the determining the fetal blood oxygen saturation, according to the respective target photoplethysmography signals determined, comprises:
determining the fetal blood oxygen saturation $SpO_2$ by using a formula below, according to the respective target photoplethysmography signals determined:

$$(SpO)_2 = \frac{\varepsilon_{RHb}^{\lambda_1}}{\varepsilon_{RHb}^{\lambda_1} - \varepsilon_{HbO_2}^{\lambda_1}} - \frac{\varepsilon_{RHb}^{\lambda_2}}{\varepsilon_{Rhb}^{\lambda_1} - \varepsilon_{HbO_2}^{\lambda_1}} * \frac{R^{\lambda_1}}{R^{\lambda_2}};$$

$$R^{\lambda_1} = \frac{\Delta I^{\lambda_1}}{I_{min}^{\lambda_1}};$$

$$R^{\lambda_2} = \frac{\Delta I^{\lambda_2}}{I_{min}^{\lambda_2}};$$

wherein $\lambda_1$ represents a first wavelength in the two wavelengths; $\lambda_2$ represents a second wavelength in the two wavelengths; $\varepsilon_{RHb}^{\lambda_1}$ represents an absorption coefficient of reduced hemoglobin in a fetal artery that corresponds to detection light of the first wavelength; $\varepsilon_{RHb}^{\lambda_2}$ represents an absorption coefficient of reduced hemoglobin in the fetal artery that corresponds to detection light of the second wavelength; $\varepsilon_{HbO_2}^{\lambda_1}$ represents an absorption coefficient of oxyhemoglobin in the fetal artery that corresponds to the detection light of the first wavelength; $\Delta I^{\lambda_1}$ represents an amplitude value of a target photoplethysmography signal corresponding to the detection light of the first wavelength; $I_{min}^{\lambda_1}$ represents a minimum value of the target photoplethysmography signal corresponding to the detection light of the first wavelength; $\Delta I^{\lambda_2}$ represents an amplitude value of the target photoplethysmography signal corresponding to the detection light of the second wavelength; and $I_{min}^{\lambda_2}$ represents a minimum value of the target photoplethysmography signal corresponding to the detection light of the second wavelength.

9. A non-transitory computer-readable storage medium, having a computer program stored thereon, wherein the computer program, when executed by a processor, implements the method for detecting fetal blood oxygen saturation according to claim 6.

10. A computer device, comprising a memory, a processor, and a computer program stored on the memory and executable by the processor, wherein the processor, when executing the computer program, implements the method for detecting fetal blood oxygen saturation according to claim 6.

11. An apparatus for detecting fetal blood oxygen saturation, comprising: a first detecting portion, a second detecting portion, and a signal processing portion;
the first detecting portion comprising: at least two first light sources and a first photoelectric volume detector, wherein each of the first light sources is configured to emit detection light of one wavelength, wavelengths of detection light emitted by respective first light sources are different from each other, and the first photoelectric volume detector is configured to receive light of the detection light that is reflected by a fetus;
the second detecting portion comprising: at least two of the first light sources and a second photoelectric volume detector, wherein the second photoelectric volume detector is configured to receive light of the detection light that is transmitted through a detection site except for an examined pregnant woman's abdomen;
the signal processing portion comprising: a first signal processor, a second signal processor, a third signal processor, and a blood oxygen saturation determining unit, wherein
the first signal processor is configured to control the respective first light sources in the first detecting portion to emit detection light in a time-sharing manner, to irradiate the fetus in the examined pregnant woman's abdomen, and acquire first photoplethysmography signals corresponding to the abdomen under irradiation of the respective wavelength of detection light, according to light of the respective wavelength of detection light that is reflected by the fetus and received by the first photoelectric volume detector;
the second signal processor is configured to control the respective first light sources in the second detecting portion to emit detection light in a time-sharing manner, to irradiate the detection site; and acquire second photoplethysmography signals corresponding to the detection site under irradiation of the respective wavelength of detection light, according to light of the detection light that is transmitted through detection sites except the detection site and received by the second photoelectric volume detector;
the third signal processor is configured to determine a target photoplethysmography signal of the fetus that corresponds to detection light of each wavelength, according to the first photoplethysmography signals and the second photoplethysmography signals that correspond to the detection light of each wavelength; and
the blood oxygen saturation determining unit is configured to determine the fetal blood oxygen saturation, according to respective target photoplethysmography signals determined,
wherein in a case of determining the target photoplethysmography signal of the fetus that corresponds to the detection light of each wavelength, according to the first photoplethysmography signals and the second photoplethysmography signals that correspond to the detection light of each wavelength, the third signal processor is configured for:
determining a target frequency domain signal of the fetus that corresponds to the detection light of each wavelength, according to the first photoplethysmography signals that correspond to the detection light of each wavelength, according to the first photoplethysmography signals and the second photoplethysmography signals that correspond to each wavelength of the detection light;
determining a corresponding fetal heart rate according to a present rule; and
determining the target photoplethysmography signal of the fetus that corresponds to the detection light of each wavelength, according to the corresponding fetal heart rate determined and respective target frequency domain signals,
wherein in a case of determining the corresponding fetal heart rate according to the present rule, the third signal processor is configured for;
determining a fetal heart rate corresponding to each wavelength of the detection light, according to the target frequency domain signal of the fetus that corresponds to each wavelength of the detection light,
wherein in a case of determining the target photoplethysmography signal of the fetus that corresponds to the detection light of each wavelength, according to the corresponding fetal heart rate determined and the respective target frequency domain signals, the third signal processor is configured for:
determining the target photoplethysmography signal of the fetus that corresponds to the detection light of each wavelength, according to the fetal heart rate and the target frequency domain signal corresponding to the detection light of each wavelength, and
wherein in a case of determining the fetal heart rate corresponding to each wavelength of the detection light, according to the target frequency domain signal of the fetus that corresponds to each wavelength of the detection light, the third signal processor is configured for:
determining the fetal heart rate corresponding to the detection light of each wavelength, according to the signal obtained after sequentially performing frequency-time conversion processing, autocorrelation processing and time-frequency conversion processing on the target frequency domain signal corresponding to the detection light of each wavelength.

* * * * *